United States Patent [19]

Bailey et al.

[11] Patent Number: 5,432,091
[45] Date of Patent: Jul. 11, 1995

[54] N-TERMINAL SEQUENCING OF PROTEINS AND PEPTIDES

[75] Inventors: Jerome M. Bailey, Duarte; John E. Shively, Arcadia, both of Calif.

[73] Assignee: City of Hope, Duarte, Calif.

[21] Appl. No.: 121,257

[22] Filed: Sep. 15, 1993

Related U.S. Application Data

[63] Continuation-in-part of Ser. No. 95,704, Jul. 22, 1993.

[51] Int. Cl.⁶ .................. A61K 38/00; C07K 1/00; C07K 17/00
[52] U.S. Cl. ........................... 436/87; 436/89; 436/90; 530/345; 530/408
[58] Field of Search ............... 436/87, 89, 90; 530/345, 408

[56] References Cited

U.S. PATENT DOCUMENTS

| | | | |
|---|---|---|---|
| 4,861,726 | 8/1989 | Stolowitz et al. | 436/89 |
| 5,240,859 | 8/1993 | Aebersold | 436/89 |

OTHER PUBLICATIONS

Zubay "Biochemistry", 2nd ed. MacMillan Publishing Co. 1988, p. 48.
Salnikow, et al., *Methods in Protein Sequence Analysis* (Ed. Elzinga, M.) Humana Press, Clifton, N.J., pp. 181–188 (1982).
Jin, S. W., et al., *FEBS Lett.* 198:34–41 (1989).
Horn, M. J., *Techniques in Protein Chemistry* (Ed., Hugli, E. T.) Academic Press, San Diego, pp. 51–58 (1989).
Margolies, M. N., et al., *Methods in Protein Sequence Analysis* (Ed. Elzinga, M.) Humana Press, Clifton, N.J. pp. 189–203 (1982).
Jin et al. FEBS Lett. vol. 198 (1986) p. 150.

*Primary Examiner*—Jill Warden
*Assistant Examiner*—Sheela J. Huff
*Attorney, Agent, or Firm*—Edward S. Irons

[57] ABSTRACT

An improved method for the N-terminal sequential degradation of proteins and peptides is disclosed. The protein or peptide to be sequenced is reacted with a compound effective to impart a tertiary amine functionality to the thiazolinone derivative of a cleaved terminal amino acid of the peptide.

4 Claims, 6 Drawing Sheets

N-Terminal Sequencing With Dimethylaminopropyl Isothiocyanate

N-TERMINAL SEQUENCING OF PROTEINS AND PEPTIDES

This application is a continuation-in-part of application Ser. No. 08/095,704 filed Jul. 22, 1993.

FIELD OF INVENTION

This invention relates to the sequential degradation of proteins and peptides from the N-terminus. More particularly, the invention relates to the sequential N-terminal degradation of peptides, including small peptide samples, which removes the N-terminal amino acid as a thiazolinone derivative which can subsequently be derivatized by an amine or hydroxy containing nucleophile containing a fluorescent group or a functional group optimal for a particular method of detection. The use of fluorescent or other methods of detection is anticipated to permit improved sensitivity of protein and peptide sequencing.

BACKGROUND OF THE INVENTION

One of the primary goals of protein chemists is to relate the function of a protein to its structure. With this goal in mind, an early step in the structural characterization of proteins is the determination of primary structure or sequence. Currently, primary structural determination can be accomplished either by sequencing the protein on an automated sequencer using the Edman chemistry for successive degradation or by sequencing the gene for that protein using established DNA sequencing methodology. Although protein sequencing can be considered to be more difficult and slower than DNA sequencing, it often provides information not obtainable by the latter method. Protein sequencing can provide information concerning post translational modifications which are not predictable from the gene sequence, such as location of proteolytic cleavage sites. Furthermore, it is a key method for the determination of protein sequence information which can be used for the design of oligonucleotide probes complementary to predicted gene sequences. In many cases, these oligonucleotide probes, obtained from protein sequence analysis, have been the only route to the cloning of a particular gene.

Currently, protein sequence analysis is primarily accomplished with the use of an automated sequencer using chemistry developed by Edman over forty years ago (1) (FIG. 1). Since that time, improvement in the instrumentation (2, 3) has resulted in the ability to sequence smaller and smaller sample quantities (mmole to pmol), although the original chemistry has remained essentially unchanged. Current automated instrumentation permits 10-20 cycles of sequence determination on 10-50 pmol of sample.

Advances in protein isolation methodology have recently made it possible to isolate proteins of biological interest which are present in tissues in sub-picomole quantities. Techniques such as 1- and 2-dimensional electrophoresis (with electroblotting to membranes), microcolumn liquid chromatography, and capillary electrophoresis have allowed protein and peptide purification down to the 10-100 femtomole level. Many of these proteins have been shown to have key roles in the development and treatment of human disease. Improved methods of protein sequencing requiring less sample quantity would make it possible to obtain the necessary sequence information in order to clone and express these proteins, thereby making it possible to study the structure function aspects of these important proteins. It is generally anticipated that this information could set the stage for advances in the treatment of human diseases through rationalized drug design and gene therapy.

A major limitation to increasing the sensitivity of protein sequencing down to the femtomolar level involves the intrinsic detectability of the released PTH amino acids. The PTH amino acids, which are detected by absorption at 269 nm, have relatively low extinction coefficients. Intrinsic background noise associated with absorbance measurements at this wavelength and chemical background from the reagents used in sequencing also contribute to the limit of detection. Although a recently published method involving the use of absorbance detection with capillary electrophoresis rather than HPLC for separation of the PTH amino acids has shown femtomolar detection (4), this technique requires subnanoliter injection volumes. Current automated sequencer technologies dissolve the PTH amino acids in a 50-200 $\mu$l volume for injection. Use of only a small fraction of this volume would negate any value in the increased sensitivity of detection using capillary electrophoresis.

Numerous attempts have been made to increase the sensitivity of Edman degradation through the use of radiolabeled, chromophoric, or fluorescent isothiocyanate reagents. 4-(N,N'-dimethylamino)azobenzene-4'-isothiocyanate (DABITC), a highly chromophoric reagent first described by Chang et al. (5) has primarily been used as a manual sequencing reagent with a DABITC/PITC double coupling procedure (6), although it has been used in automated solid-phase sequencing (7). More recently, Aebersold et al. (8, 9) reported a DABITC solid-phase sequencing method in which proteins were immobilized on DITC-derivatized aminopropyl glass-fiber sheets. Sequence analysis was performed at the 20-50 picomole level, a substantial improvement over previous methods, but sill less sensitive than current gas-phase sequence analysis. Fluorescent reagents, such as fluorescein isothiocyanate (10, 11) and dansyl-containing isothiocyanates (12-16) have also been evaluated as sensitivity enhancing reagents. Although synthetic amino acid derivatives prepared using these reagents show subpicomole sensitivity by HPLC analysis, they have not surpassed the sensitivity of gas-phase Edman degradation during automated sequence analysis. In general, it has been found that the use of large bulky chromophores on the isothiocyanate reagent interferes with the efficiency of the derivatization and cleavage reactions of the Edman degradation. The inhibition of the coupling and cleavage reactions with these reagents is postulated to be caused by a combination of steric and electronic effects. The use of radiolabeled reagents has also proven not to be successful, since radiolabeled reagents undergo autoradiodegradation which results in decreasing product yields and increasing amounts of labeled by-products. Modified phenyl isothiocyanates such as 4-(Boc-aminomethyl)-PITC, which are designed to react with post-column fluorescent reagents, have also been investigated (17) but have been found to undergo side reactions during the cleavage reaction resulting in loss of the amino group (14).

An alternative to the use of modified Edman reagents is the reaction of the anilinothiazolinone (ATZ)-amino acid intermediate with sensitivity-enhancing nucleophilic reagents. The use of radiolabeled amines produced amino acid derivatives which could be detected at the femtomole level (18, 19), but the handling of radioactive materials was inconvenient. Horn et al. (20) have extended earlier studies on the use of MeOH/HCL as a conversion reagent (21) to include chromophoric or fluorophoric alcohols, resulting in the formation of phenylthiocarbamyl amino acid esters. Tsugita et al. (22) have recently reported a modification of the Edman degradation scheme, in which ATZ amino acids are reacted with 4-aminofluorescein resulting in highly fluorescent, phenylthiocarbamyl amino acid aminofluorescein amides (PTCAF-amino acids) (FIG. 2). PTCAF-amino acids were separated by reversed-phase HPLC and were detectable at the 0.1–1 femtomole level. Several known and unknown protein samples were reported to be sequenced at the 100 femtomole to 10 picomole level using an Applied Biosystems 477A sequencer. An experiment based on the chemistry shown in FIG. 2 resulted in the data reflected by FIG. 3.

Sequencing of β-lactoglobulin and a synthetic peptide was performed at the 5–10 picomole level. 5.5 picomoles of β-lactoglobulin was spotted on a $1 \times 10$ mm piece of Polybrene-coated PVDF and inserted into a reaction cartridge for sequence analysis. Approximate initial and repetitive yields of 50% and 96%, respectively, were observed. Poor yields were seen for threonine (cycles 4 and 6). Aspartic acid (cycle 11) was not observed (it is shown as 0.1 picomoles for graphing purposes only). The computer generated line in FIG. 3 appears to have the correct slope although it is placed rather low on the graph. This is most likely due to the low yields on the threonine and aspartic acid cycles. One major background peak (~3 picomole equivalents) was seen with several minor background peaks of <1 picomole equivalent. By extrapolation, the most sensitive detector setting would be expected to permit sequence analysis at the 10–100 femtomole level.

Conclusions from this work show that this approach suffers from a number of problems which make it of little practical value toward the goal of more sensitive sequencing. The most serious difficulty with this method, in its present form, is the low yields obtained with the hydrophilic amino acids, in particular threonine, histidine, glutamate, lysine, and glutamine, and the total lack of yield obtained with aspartate. Recent studies concerning the aminolysis of the ATZ-amino acids by Pavlik et al. (23), showed that many of the ATZ-amino acids, in particular the hydrophilic amino acids, can rearrange so rapidly to the more thermodynamically stable PTH amino acids that by the time the ATZ-amino acid is brought over to the conversion flask of an automated instrument anywhere from 5–70% of the amino acid has already been converted. Once an ATZ-amino acid has converted to a PTH it would not be capable of reacting with aminofluorescein. This explanation is consistent with observed data. By analogy with the data presented above, it is anticipated that any chemical scheme that relies on tagging the ATZ analogue with a fluorescent molecule, such as reaction of the ATZ analogues with alcohols (20), will not offer any practical gains in the sensitivity of N-terminal microsequencing.

The present status of microsequence analysis, protein and peptide purification, and other related techniques was the subject of a recent review (24) and a number of recent monographs (25–30). It was concluded that improvement in analytical techniques such as microsequence analysis was necessary in order to match the capability of the purification methods. Improvements in microsequence analysis could have far reaching effects. For example, the ability to detect differences in complex biological samples such as cerebrospinal fluid by 2D-electrophoresis (31) and also obtain meaningful sequence information could be of great importance in understanding various pathological states.

SUMMARY OF THE INVENTION

This invention provides an improvement in method for the sequential degradation of proteins and peptides in which a thiourea derivative is treated with acid to provide a thiazolinone derivative of the cleaved terminal amino acid. The improvement comprises reacting the protein or peptide to be sequenced with a compound effective to impart a tertiary amine functionality to such thiazolinone derivatives. The tertiary amine functionality stabilizes the thiazolinone derivative against rearrangement to a thiohydantoin, thus facilitating derivatization of said stabilized thiazolinone with a nucleophilic amino or hydroxyl containing fluorophore.

The tertiary amine functionality may be imparted to the thiazolinone derivatives in a single step procedure with an appropriate isothiocyanate or in a two step procedure which entails sequential reaction of the thiazolinone derivative with a thiocarbonyl compound and a nucleophile. The methods of the invention are readily automated using presently available instrumentation.

DETAILED DESCRIPTION OF THE INVENTION

The vast majority of reagents that have been utilized to place a fluorescent or highly chromophoric tag on the released thiohydantoin amino acid have relied on the isothiocyanate group as the electrophilic group used to mediate the coupling reaction. Isothiocyanates form a thiourea group with the N-terminal amino acid. The sulfur atom of the thiourea is thus perfectly placed so that upon acidification a kinetically favored five-membered thiazolinone ring could form which specifically cleaves only the N-terminal amino acid. Most chromophoric and fluorescent compounds are relatively large when compared to the phenyl ring of phenyl isothiocyanate (PITC, the reagent commonly used for N-terminal protein sequencing). Typically, when a large chromomophoric compound that contains a reactive isothiocyanate group is substituted for PITC, the coupling and/or cleavage reaction is kinetically disfavored by a combination of steric and electronic effects. This results in poor initial and repetitive yields of sequencing.

Figure 1:
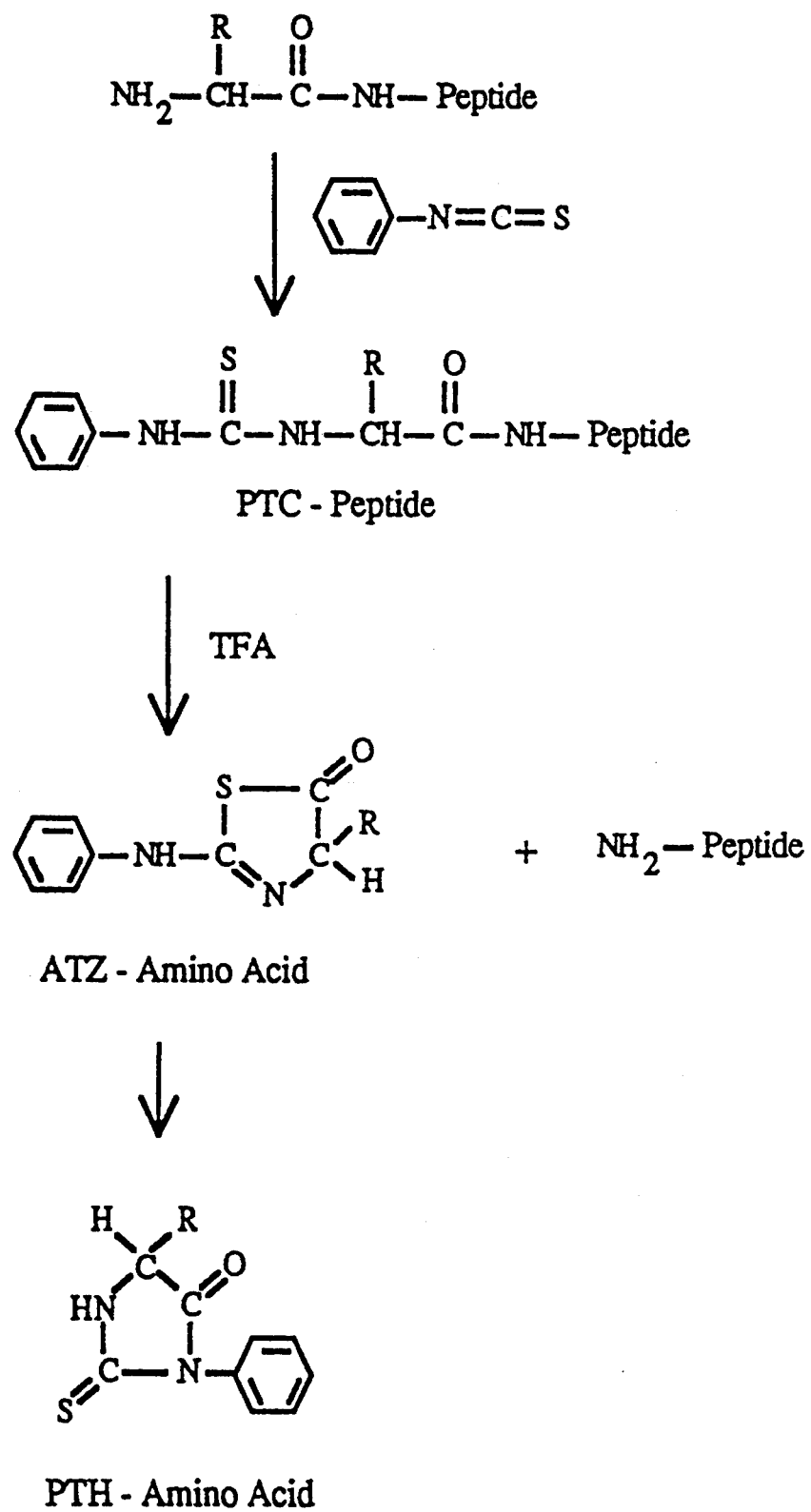
FIG. 1 illustrates Edman chemistry for N-terminal sequencing.
Figure 2:
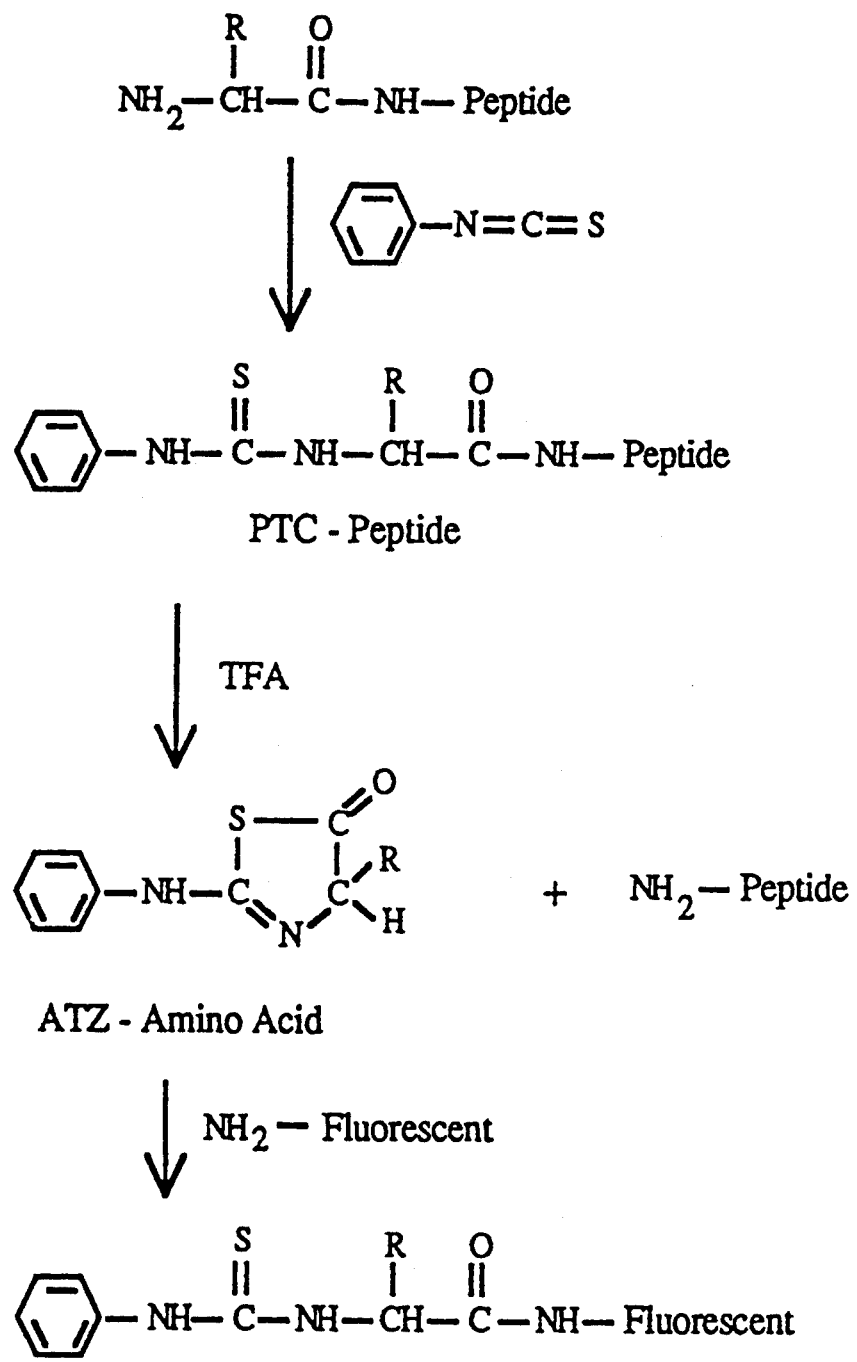
FIG. 2 illustrates N-terminal sequencing chemistry in which an ATZ-amino acid is reacted with a fluorescent amine.
Figure 3:
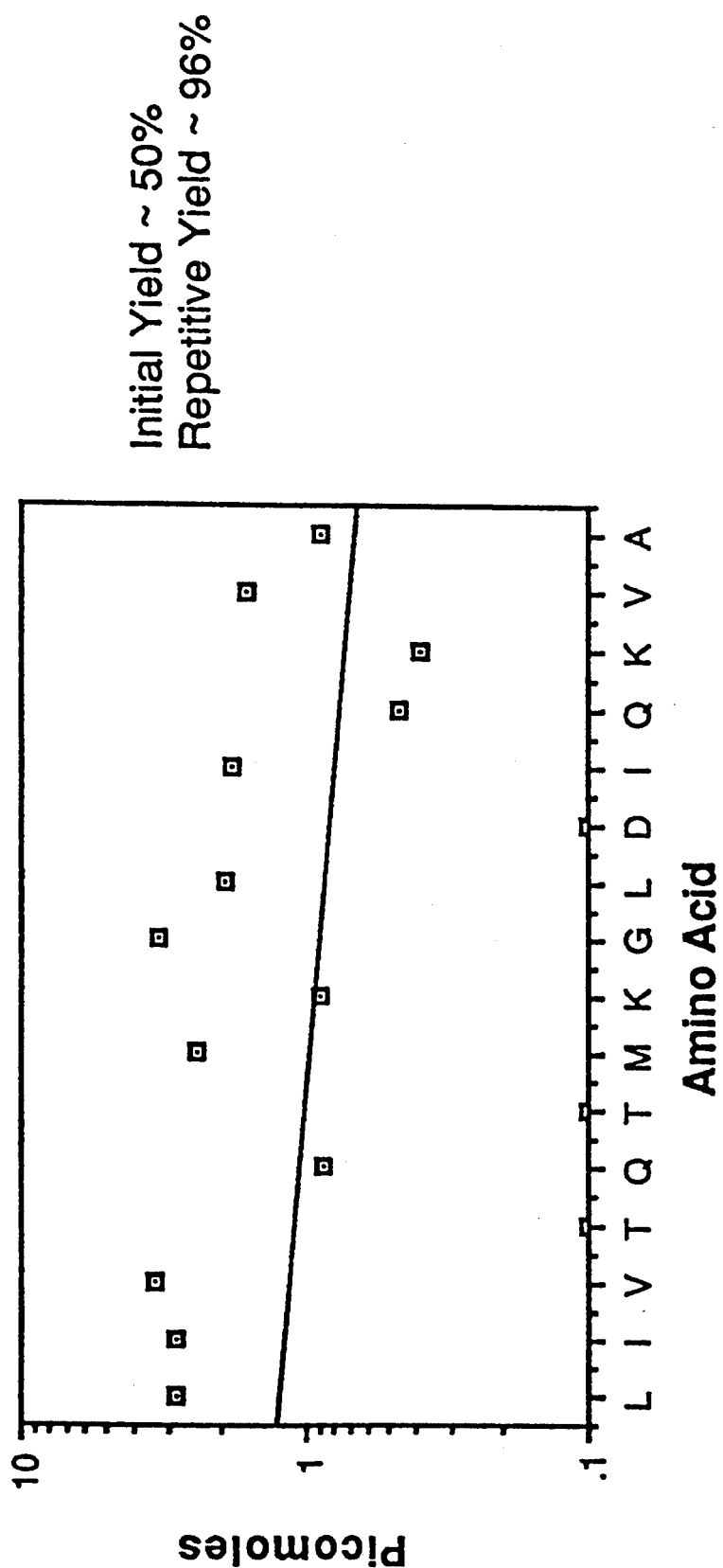
FIG. 3 is a repetitive yield plot for gas-phase sequence analysis of β-lactoglobulin (5.5 picomoles loaded) using aminofluorescein derivatization of ATZ-amino acids.

An alternative procedure for introducing a fluorescent or chromophoric tag onto the released amino acid has relied upon reaction of the anilinothiazolinone (ATZ) analogue (FIG. 1), formed during the normal Edman degradation, with a nucleophilic amine (22) or fluorescent alcohol (20). Both of these techniques assume that the thiazolinone analogue formed during sequencing is stable long enough for the nucleophilic chromophore to be added. However, in actual practice, this assumption has turned out not to be entirely true. A recent study (23) has shown that in fact a significant portion of the ATZ amino acids immediately rearrange to their more thermodynamically stable thiohydantoin analogues. Once the thiohydantoin analogue has formed, it can no longer be reacted with a nucleophilic tag to form the desired fluorescent derivative. This rearrangement to the more thermodynamically stable thiohydantoin was observed to be more pronounced with the more hydrophilic amino acids. This observation is consistent with the data observed when automated sequencing was performed with the aminofluorescein procedure described by Tsugita et al. (22). The yields of sequencing obtained with the hydrophilic amino acids were poor and nonexistent for aspartic acid. By contrast the yields obtained with the hydrophobic amino acids were observed to be good.

In general, it can be concluded that reaction of the thiazolinone derivative obtained during normal Edman chemistry with a nucleophilic amine or hydroxyl molecule containing a fluorescent or chromophoric tag will not be a practical method for increasing the sensitivity of N-terminal sequence analysis (to require less sample for analysis) since the thiazolinone derivative of the hydrophilic amino acids, especially aspartate, rearranges too rapidly to the unreactive thiohydantoin derivative and therefore prevents efficient tagging of these amino acids.

One method to solve this problem is to produce during sequencing, a thiazolinone derivative which will not so readily rearrange to a thiohydantoin derivative and thus would be capable of quantitative derivatization with an amine or hydroxyl nucleophile containing a chromophoric or fluorescent group. This invention entails the formation of such a stable thiazolinone and subsequent tagging with a group optimal for various methods of detection.

Figure 4:
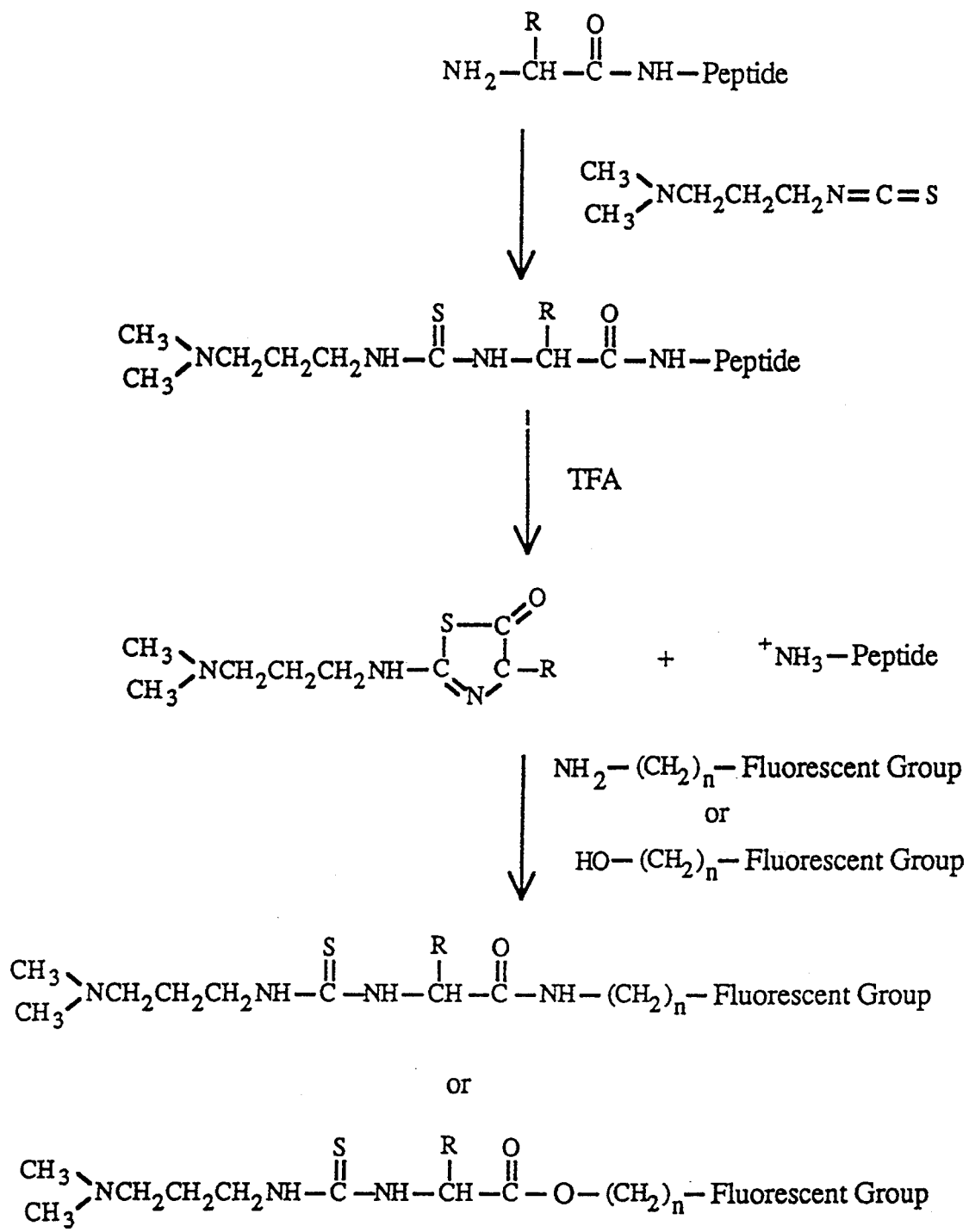
FIG. 4 illustrates N-terminal sequencing with dimethylaminopropyl isothiocyanate.

The stable thiazolinone provided by this invention is one which contains in place of the phenyl group (in currently practiced methods of N-terminal sequence analysis), a group which contains a tertiary amine function. Such a functionality has been found to stabilize the thiazolinone formed, thus permitting the quantitative derivatization of such a thiazolinone with a nucleophilic amino or a hydroxyl containing fluorophore. There are two major methods for forming such a thiazolinone. The first is outlined in FIG. 4. The N-terminal amino acid of a peptide or protein is derivatized with an isothiocyanate having a tertiary amine function. The derivatized peptide is cleaved in known manner, e.g., with trifluoroacetic acid (TFA) to form a thiazolinone derivative. The thiazolinone derivative so formed is then treated with an amino or hydroxyl containing nucleophile which contains a group optimal for detection. For example, a fluorophore for fluorescent detection or a highly chromophoric reagent for ultraviolet or visible absorbance detection.

The amino isothiocyanate reagents having a tertiary amino function which are useful for this aspect of the invention are represented by Formula 1:

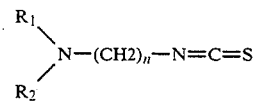

in which $R_1$ and $R_2$ are independently the same or different alkyl groups 1 to 15 carbon atoms in length or the same or different substituted or unsubstituted phenyl groups. $R_1$ and $R_2$ in combination may be $CH_2$ groups in a heterocyclic compound such as a pyridine. n is from 1 to 15. The preferred reagent is dimethylaminopropyl isothiocyanate:

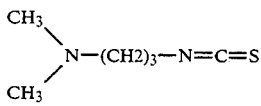

The protein or peptide to be sequenced can either be covalently or non-covalently attached to various solid supports currently used in the field. Examples include PVDF, glass fiber filters, silica beads, polyethylene, carboxyl modified polyethylene or PVDF, and porous polytetrafluoroethylene (Zitex). The peptide or protein is then derivatized with dimethylaminopropyl isothiocyanate or similar reagent to form a peptidyl derivative. The cleavage reaction is then performed with liquid or gaseous trifluoroacetic acid or other acid such as hydrochloric acid to form the thiazolinone amino acid. Trifluoroacetic acid is preferred. The thiazolinone so formed is then treated with a fluorescent amine or fluorescent alcohol. Examples of suitable fluorescent derivatives include dansyl cadaverine, aminofluorescein, fluorenylmethyl alcohol, and 9-anthracenemethanol. Fluorenylmethyl alcohol is the preferred reagent.

Figure 5:
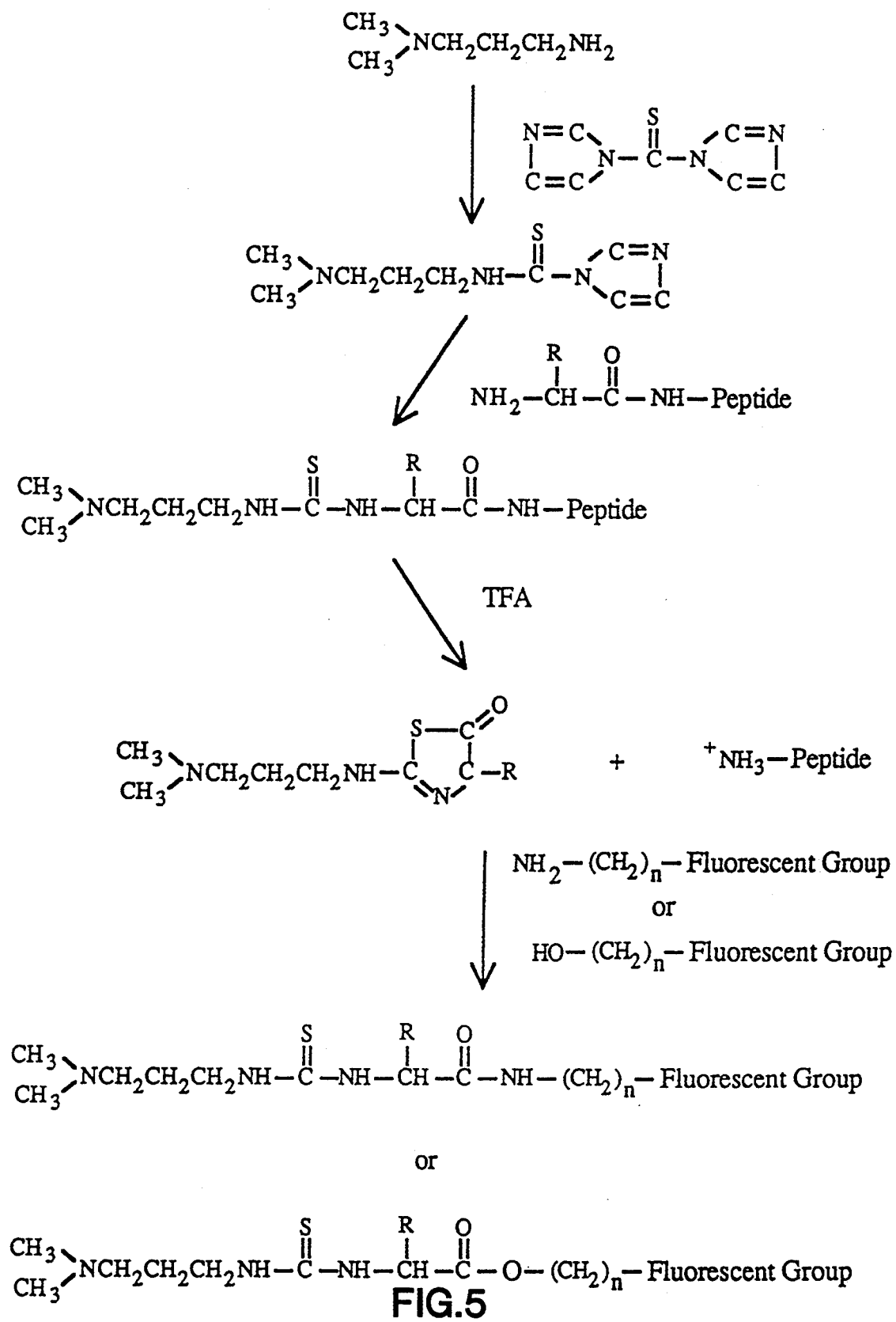
FIG. 5 illustrates the two step procedure of the invention for imparting a stabilizing tertiary amino functionality to the thiazolinone derivative of the N-terminal amino acid of a protein or peptide.

The second method for forming the same stable thiazolinone derivative is based on an alternative two-step chemistry which utilizes an electrophilic molecule, such as 1,1'-thiocarbonyldiimidazole or di-2-pyridyl thionocarbonate, to place the thiocarbonyl moiety at the N-terminus (FIG. 5). In the practice of the invention, a primary amine nucleophile containing the desired functional group is reacted in equimolar quantity with an electrophilic thiocarbonyl, such as 1,1'-thiocarbonyldiimidazole. The resulting unsymmetrical thiourea is then reacted with the N-terminal amine of a protein or peptide to produce a thiourea at the N-terminus of that protein or peptide which contains the desired functional group. As described above, treatment of this derivatized protein or peptide with acid then causes the simultaneous cleavage and cyclization of the N-terminal amino acid to form a stable thiazolinone derivative which can be derivatized with a nucleophilic amine or hydroxyl group as described above.

Primary amine nucleophiles useful in the invention are represented by Formula 2:

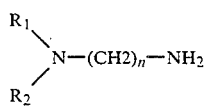

in which $R_1$ and $R_2$ are independently the same or different alkyl groups 1 to 15 carbon atoms in length or the same or different substituted or unsubstituted phenyl groups. $R_1$ and $R_2$ in combination may also be $CH_2$ groups in a heterocyclic compound such a pyridine. n may be from 1 to 15. The amines which have so far been successfully tested are dimethylaminopropylamine, dimethylaminoethylamine, diethylaminopropylamine and dibutylaminopropylamine. The preferred reagent is dimethylaminopropylamine:

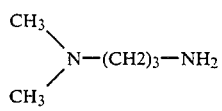

Pursuant to this invention the thiazolinone formed is derivatized with any number of groups which could then be utilized to permit many different types of detection in addition to fluorescence or ultraviolet. Such examples include mass spectrometry, chemiluminescence, and electron capture.

EXEMPLIFICATION OF THE INVENTION

EXAMPLE I

Figure 6:
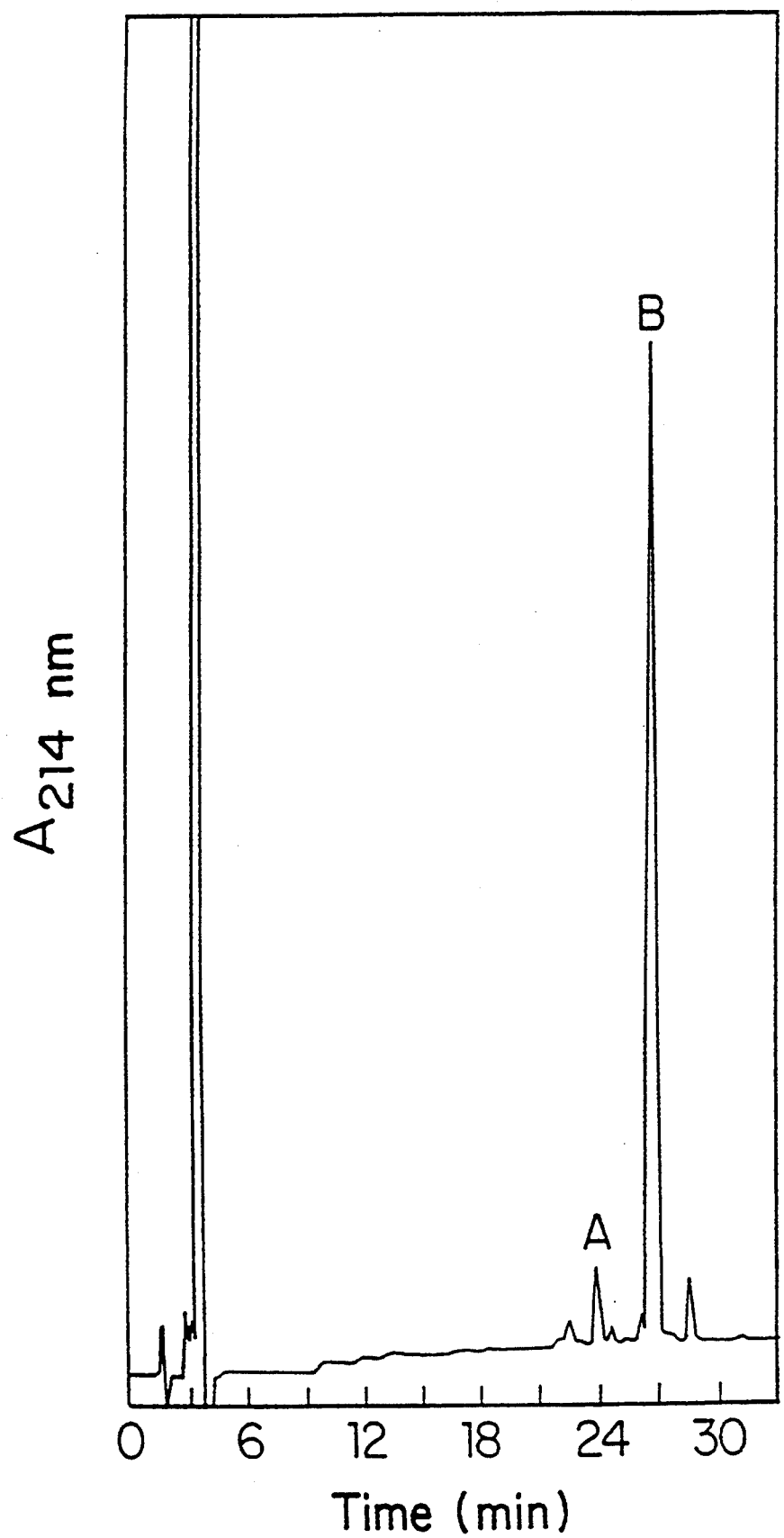
FIG. 6 is a reversed-phase HPLC chromatographic analysis of the product of the two step embodiment of the invention.

Reaction of YGGFL with Dimethylaminopropylamine and Thiocarbonyldiimidazole. Dimethylaminopropylamine (1 μmol in 50 μl of DMF) was added to 1,1'-thiocarbonyldiimidazole (1 μmol in 50 μl DMF) and allowed to react for five minutes at 25° C. The pentapeptide, YGGFL (100 nmol in 50 μl DMF), was added and allowed to react for twenty minutes at 25° C. The sample was then taken to dryness in a vacuum centrifuge, redissolved in 0.1% trifluoroacetic acid in water (100 μl), and analyzed by reversed phase HPLC (FIG. 6). The expected peptide product (the N-terminal dimethylaminopropylthiourea derivative; peak B) was identified by FAB/MS (MH+ =700) and obtained in approximately 95% yield. Peak A is the starting peptide, YGGFL (MH+ =556). Peak B was then treated with 50 μl of anhydrous trifluoroacetic acid for ten minutes at 50° C., dried in a vacuum centrifuge, redissolved in 0.1% trifluoroacetic acid in water (100 μl), and analyzed by reversed phase HPLC. The shortened peptide (GGFL) (MH+ =393) and the dimethylaminopropyl thiocarbamyl amino acid (MH+ =326) were found in quantitative yield. No dimethylaminopropyl thiohydantoin tyrosine was obtained.

Reaction of Dimethylaminopropyl Thiazolinone Tyrosine with Methanol. In a separate experiment, the dried TFA cleavage reaction from above was dissolved in 100 μl methanol and incubated for ten minutes at 50° C. The reaction was taken to dryness, redissolved in 0.1% trifluoroacetic acid in water (100 μl), and analyzed by reversed phase HPLC. The shortened peptide (GGFL) (MH+ =393) and the dimethylaminopropyl thiocarbamyl tyrosine methyl ester (MH+ =340) were found in quantitative yield.

EXAMPLE II

Reaction of the tripeptide, DYM, with Dimethylaminopropylamine and Thiocarbonyldiimidazole. Dimethylaminopropylamine (1 μmol in 50 μl DMF) was added to 1,1'-thiocarbonyldiimidazole (1 μmol in 50 μl DMF) and allowed to react for five minutes at 25° C. The tripeptide, DYM (100 nmol in 50 μl DMF), was added and allowed to react for twenty minutes at 25° C. The sample was then taken to dryness in a vacuum centrifuge, redissolved in 0.1% trifluoroacetic acid in water (100 μl), and analyzed by reversed phase HPLC. The expected peptide product (the N-terminal dimethylaminopropylthiourea derivative) was identified by FAB/MS (MH+ =572) and obtained in approximately 95% yield. The derivatized peptide was then treated with 50 μl of anhydrous trifluoroacetic acid for ten minutes at 50° C., dried in a vacuum centrifuge, redissolved in 0.1% trifluoroacetic acid in water (100 μl), and analyzed by reversed phase HPLC. The shortened peptide (YM) (MH+ =313) was found in quantitative yield and the dimethylaminopropyl thiocarbamyl amino acid (MH+ =278) was formed in 95-98% yield. The dimethylaminopropyl thiohydantoin aspartate (MH+ =260) was obtained at 2-5% yield.

Reaction of Dimethylaminopropyl Thiazolinone Aspartate with Methanol. In a separate experiment, the dried TFA cleavage reaction from above was dissolved in 100 μl methanol and incubated for ten minutes at 50° C. The reaction was taken to dryness, redissolved in 0.1% trifluoroacetic acid in water (100 μl), and analyzed by reversed phase HPLC. The shortened peptide (YM) (MH+ =313) was found in quantitative yield and the dimethylaminopropyl thiocarbamyl aspartate methyl ester (MH+ =292) was formed in approximately 95% yield.

Reaction of Dimethylaminopropyl Thiazolinone Aspartate with Dimethylaminopropylamine. In a separate experiment, the dried TFA cleavage reaction the DYM peptide was dissolved in 100 μl acetonitrile containing 50 μl of dimethylaminopropylamine and incubated for ten minutes at 50° C. The reaction was taken to dryness, redissolved in 0.1% trifluoroacetic acid in water (100 μl), and analyzed by reversed phase HPLC. The shortened peptide (YM) (MH+ =313) was found in quantitative yield and the dimethylaminopropyl thiocarbamyl aspartate (dimethylaminopropyl)amide (MH+ =362) was formed in approximately 95% yield.

Reaction of Dimethylaminopropyl Thiazolinone Aspartate with Fluorenylmethyl Alcohol. In a separate experiment, the dried TFA cleavage reaction the DYM peptide was dissolved in 50 μl TFA containing 500 nmole of fluorenylmethyl alcohol and incubated for ten minutes at 50° C. The reaction was taken to dryness, redissolved in 0.1% trifluoroacetic acid in water (100 μl), and analyzed by reversed phase HPLC. The shortened peptide (YM) (MH+ =313) and the dimethylaminopropyl thiocarbamyl aspartate fluorenylmethyl ester (MH+ =456) were formed in quantitative yield.

BIBLIOGRAPHY

1. Edman, P. *Acta Chem. Scand.* 4:283–293 (1950)
2. Edman P., et al. *Eur. J. Biochem.* 1:80–91 (1967)
3. Hewick, R. M., et al., *J. Biol. Chem.* 256:7990–7997 (1981)
4. Waldron, K. C., et al., *Anal. Chem.* 64:1396–1399 (1992)
5. Chang, J. Y., et al., *Biochem. J.* 153:607–611 (1976)
6. Chang, J. Y., et al., *FEBS Lett.* 93:205–214 (1978)

7. Salnikow, J., et al. *Methods in Protein Sequence Analysis* (Ed. Elzinga, M.) Humana Press, Clifton, N.J., pp. 181–188 (1982)

8. Aebersold, R. H., et al., *Biochemistry* 27:6860–6867 (1988)

9. Aebersold, R. H., et al., *Methods in Protein Sequence Analysis* (Ed. Wittmann-Liebold, B.) Springer-Verlag, Berlin, pp. 79–97 (1989)

10. Maeda, H., et al. *Biochem. Biophys. Res. Commun.* 31: 188–192 (1968)

11. Muramoto, K., *Anal. Biochem.* 141:446–450 (1984)

12. Hirano, H., *Biol. Chem. Hoppe-Seyler* 367:1259–1265 (1986)

13. Hirano, H., et al., *Methods in Protein Sequence Analysis* (Ed. Wittmann-Liebold, B.) Springer-Verlag, Berlin, pp. 42–51 (1989)

14. Jin, S. W., et al., *FEBS Lett.* 198:150–154 (1986)

15. Jin, S. W., et al., *FEBS Lett.* 198:34–41 (1989)

16. Salnikow, J., et al. *Methods in Protein Sequence Analysis*-1986 (Ed. Walsh, K. A.) Humana Press, Clifton, N.J., pp. 247–260 (1987)

17. L'Italien, J. J., et al., *J. Chromatogr.* 283:149–156 (1984)

18. Inman, J. K., *Methods Enzymol.* 47:374–385 (1977)

19. Tsugita, A., et al., *J. Biochem.* 103:399–401 (1988)

20. Horn, M. J. *Techniques in Protein Chemistry* (Ed. Hugli, E. T.) Academic Press, San Diego, pp. 51–58 (1989)

21. Margolies, M. N., et al., *Methods in Protein Sequence Analysis* (Ed. Elzinga, M.) Humana Press, Clifton, N.J., pp. 189–203 (1982)

22. Tsugita, A., et al., *J. Biochem.* 106:60–65 (1989)

23. Pavlik, M., et al., *Anal. Biochem.* 201:9–16 (1992)

24. Simpson, R. J., et al., *Anal. Biochem.* 177:221–236 (1989)

25. Hugli, T. E. Ed. *Techniques in Protein Chemistry* Academic Press, San Diego, (1989)

26. L'Italien, J. J., Ed. *Proteins: Structure and Function*, Plenum Press, New York (1987)

27. Matsudaira, P. T. Ed. *A Practical Guide to Protein and Peptide Purification for Microsequencing*, Academic Press, San Diego (1989)

28. Shively, J. E. Ed. *Methods of Protein Microcharacterization*, Humana Press, Clifton, N.J. (1986)

29. Walsh, K. A. Ed, *Methods in Protein Sequence Analysis*-1986, Humana Press, Clifton, N.J. (1987)

30. Wittmann-Liebold, B. Ed, *Methods in Protein Sequence Analysis* Springer-Verlag, Berlin (1989)

31. Merril, C. R., et al., *Science* 211:1437–1438 (1981)

We claim:

1. In a method for N-terminal sequencing in which a thiazolinone derivative of the N-terminal amino acid of a peptide or protein is formed, the improvement which comprises reacting said peptide to be sequenced with a compound effective to impart a tertiary amine functionality to said thiazolinone derivative of said N-terminal amino acid, wherein said thiazolinone derivative is stabilized with respect to rearrangement to a thiohydantoin derivative of said peptide, and wherein said stabilized thiazolinone derivative may be substantially quantitatively derivatized with a nucleophilic amino or hydroxyl containing fluorophore.

2. A method as defined by claim 1 in which said stabilized thiazolinone derivative is produced by
   (i) first reacting a primary amine nucelophile containing a preselected functional group with at least an equimolar quantity of an electrophilic thiocarbonyl to produce an unsymmetrical thiourea thereafter,
   (ii) reacting said unsymmetrical thiourea with the N-terminus group of a peptide to be sequenced to produce at said N-terminus a thiourea that contains said preselected functional group, and
   (iii) treating the thiourea product of step (ii) with acid to cause simultaneous cleavage and cyclization of the N-terminal amino acid of said peptide to be sequenced, so as to provide a stabilized thiazolinone which may be substantially quantitatively derivatized with a nucleophilic amino or hydroxyl containing fluorophore.

3. In a method for N-terminal sequencing in which a thiazolinone derivative of the N-terminal amino acid of a peptide or protein is formed, the improvement which comprises reacting said peptide to be sequenced with dimethylaminopropylamine to impart a tertiary amine functionality to said thiazolinone derivative of said N-terminal amino acid, wherein said thiazolinone derivative is stabilized with respect to rearrangement to a thiohydantoin derivative of said peptide, and wherein said stabilized thiazolinone derivative may be substantially quantitatively derivatized with a nucleophilic amino or hydroxyl containing fluorophore.

4. A method as defined by claim 1 in which said stabilized thiazolinone derivative is produced by first derivatizing said peptide to be sequenced with an isothiocyanate having a tertiary amine function to provide a thiourea derivative of said protein or peptide having said tertiary amine function of said isothiocyanate and treating said thiourea derivative having said tertiary amine function with an acid to provide a stabilized thiazolinone derivative of the N-terminal amino acid of said peptide or protein.

* * * * *